US00PP20798P2

(12) United States Plant Patent

Fransen

(10) Patent No.: US PP20,798 P2

(45) Date of Patent: Mar. 2, 2010

(54) *HOSTA* PLANT NAMED 'PARADISE ISLAND'

(50) Latin Name: *Hosta hybrida*
Varietal Denomination: Paradise Island

(76) Inventor: Marco Fransen, Paradijsweg 5, Ter Aar, 2461 TK (NL)

( * ) Notice: Subject to any disclaimer, the term of this patent is extended or adjusted under 35 U.S.C. 154(b) by 0 days.

(21) Appl. No.: 12/231,486

(22) Filed: Sep. 3, 2008

(51) Int. Cl.
*A01H 5/00* (2006.01)

(52) U.S. Cl. ..... Plt./353

(58) Field of Classification Search ..... Plt./353
See application file for complete search history.

*Primary Examiner*—Annette H. Para
*Assistant Examiner*—Louanne C Krawczewicz Myers
(74) *Attorney, Agent, or Firm*—Penny J. Aquirre

(57) ABSTRACT

A new cultivar of *Hosta* named 'Paradise Island', a sport of *Hosta* 'Fire Island', that is characterized by its unique variegated foliage with bright yellow to yellow- centers and dark green margins, its red petioles and red markings extending into the leaf blade and its lavender flowers present in early to mid summer.

3 Drawing Sheets

Botanical classification: *Hosta hybrida.*
Cultivar designation: 'Paradise Island'.

BACKGROUND OF THE INVENTION

The present invention, *Hosta* 'Paradise Island', relates to a new and distinct cultivar of *Hosta*, botanically known as a *Hosta* hybrid, hereinafter referred to as 'Paradise Island'.

The Inventor discovered the new cultivar, 'Paradise Island', in a container in his nursery in August of 2003 in Ter Aar, The Netherlands. 'Paradise Island' originated as a naturally occurring chimeral mutation of *Hosta* 'Fire Island' (unpatented).

Asexual reproduction of the new cultivar was first accomplished under the direction of the Inventor utilizing in vitro propagation in Reeuwijk, The Netherlands in September of 2005. Asexual reproduction of the new cultivar by division and tissue culture has shown that the unique features of 'Paradise Island' are stable and reproduced true to type in successive generations.

SUMMARY OF THE INVENTION

The following traits have been repeatedly observed in trials in Minnesota for a period of five years and represent the characteristics of the new cultivar. These attributes in combination distinguish 'Paradise Island' as a new and unique cultivar of *Hosta.*

1. 'Paradise Island' exhibits foliage that is variegated with bright yellow centers and dark green margins. As the season progresses, the centers become yellow-green in color with the margins remaining dark green.
2. 'Paradise Island' exhibits upright held red leaf petioles with the red coloration extending into the leaf blade.
3. 'Paradise Island' blooms in early to mid summer with lavender flowers.

The parent plant, *Hosta* 'Fire Island', has foliage that non-variegated with yellow to yellow-green foliage and red petioles. The closest comparison plant is 'Eye Declare', which has similar leaf variegation and coloration but 'Eye Declare' differs in having petioles and leaf blades that are green and lack the red coloration as observed with 'Paradise Island'.

BRIEF DESCRIPTION OF THE DRAWING

The accompanying colored photographs illustrate the overall appearance and distinct characteristics of the new *Hosta*, 'Paradise Island'. The photographs were taken of 1 year old plants as grown as grown outdoors in Ter Aar, The Netherlands.

Figure 1:
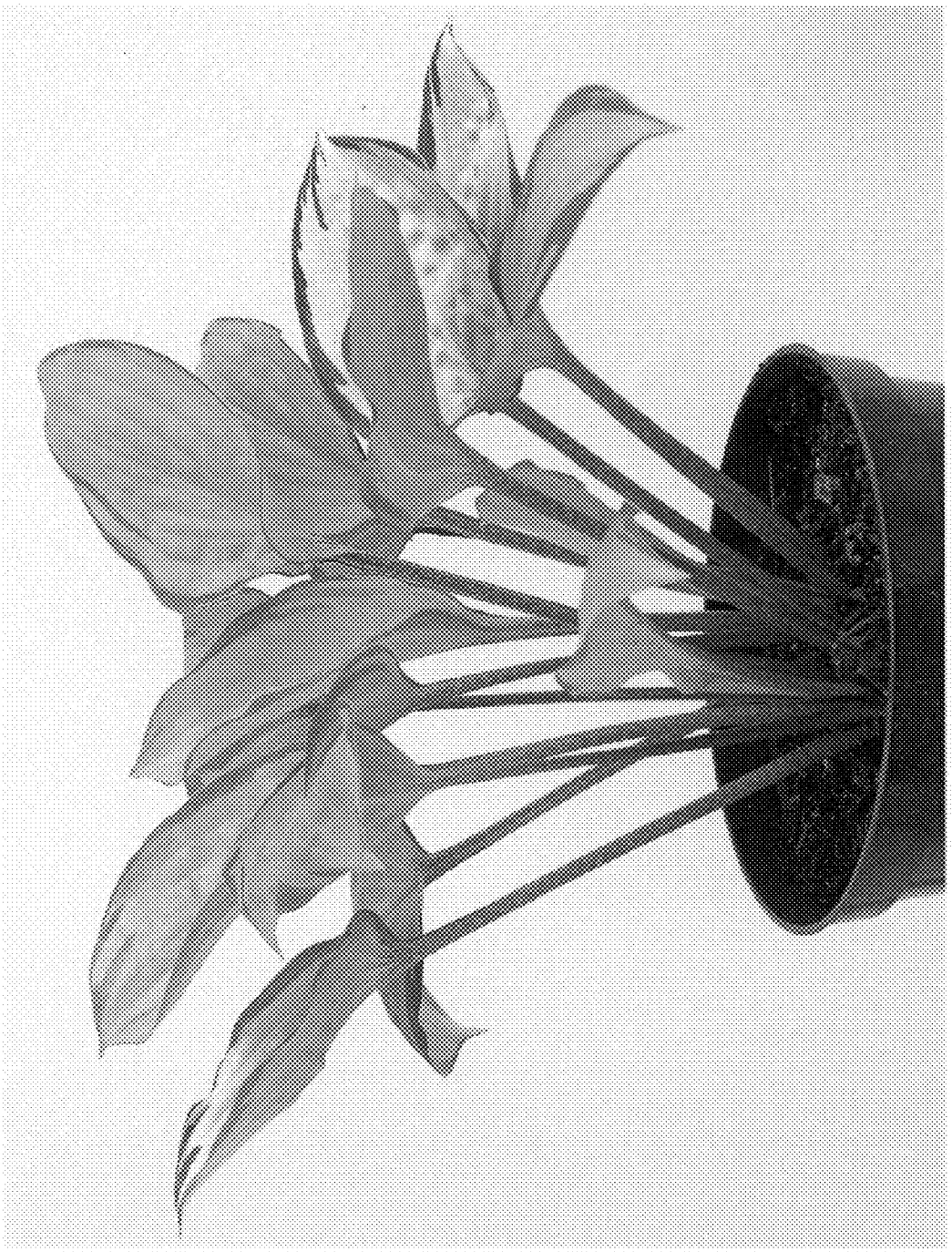
FIG. 1 provides an overall view of the foliage and plant habit of the new cultivar.
Figure 3:
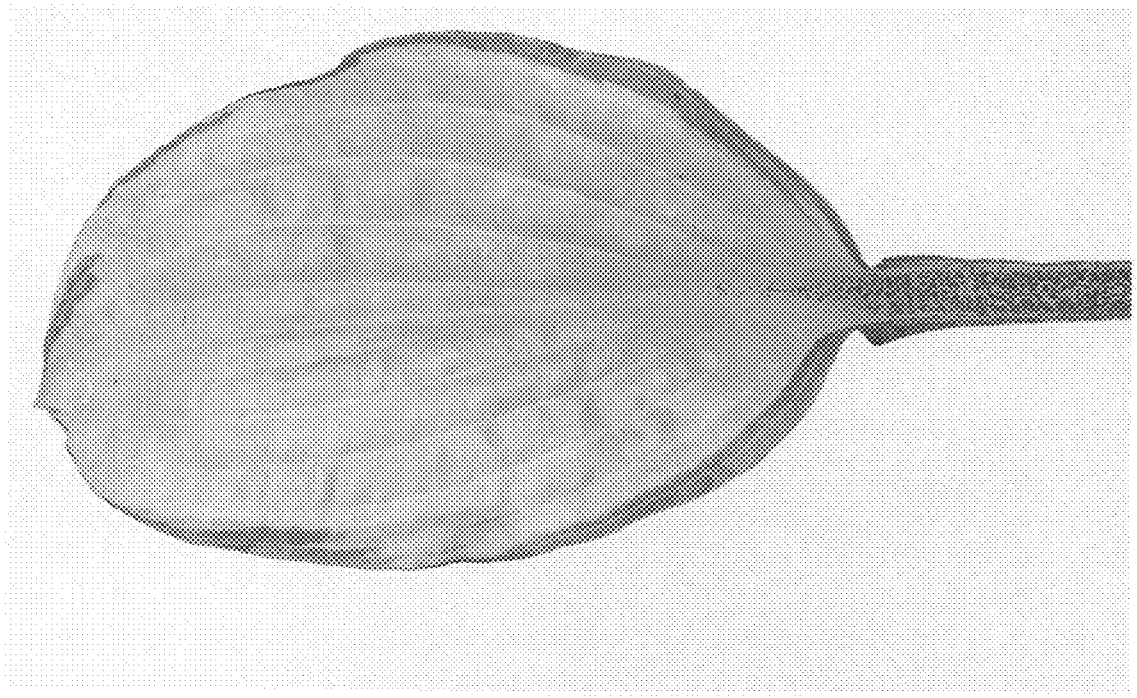
Figure 2:
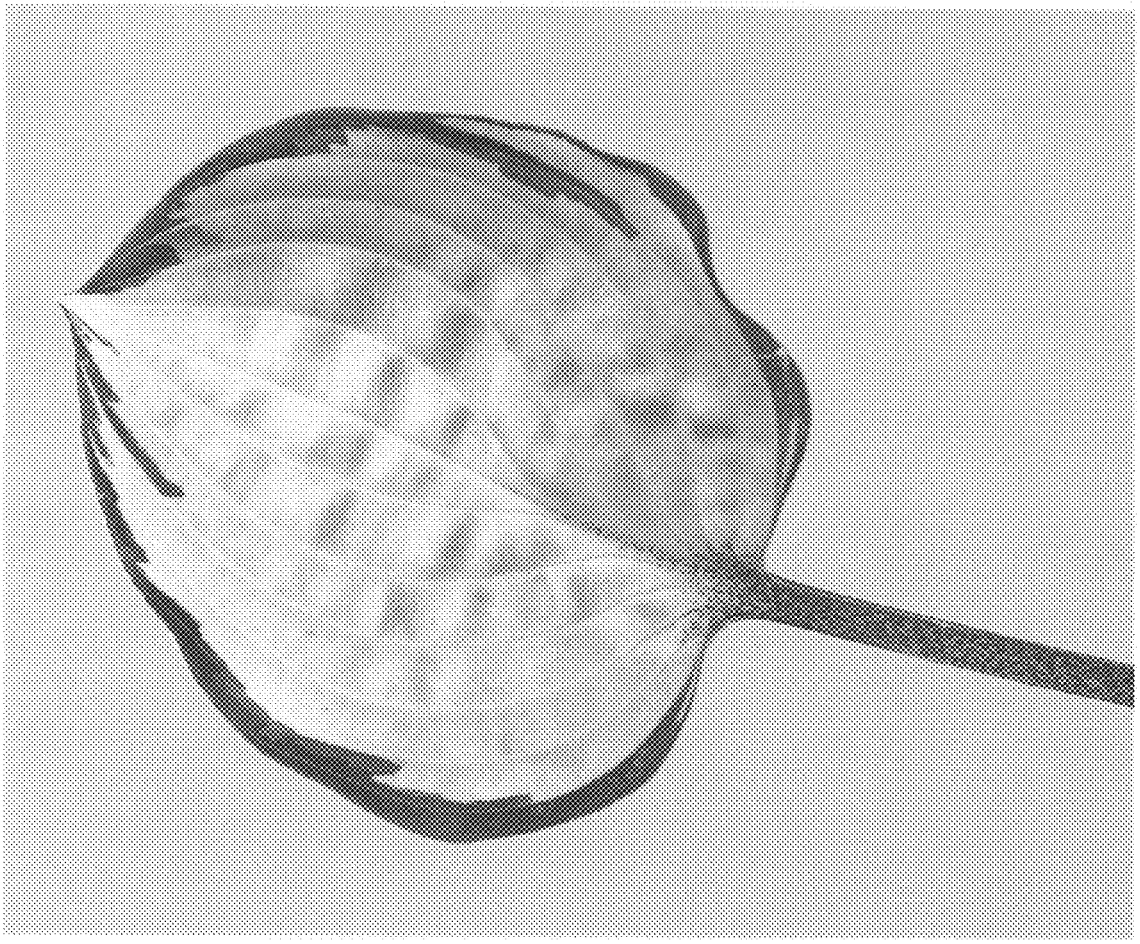

The photograph in FIG. 2 provides a close-up view of a newly emerged leaf and petiole while the photograph in FIG. 3 provides a close-up view of a mature leaf and petiole.

Figure 4:
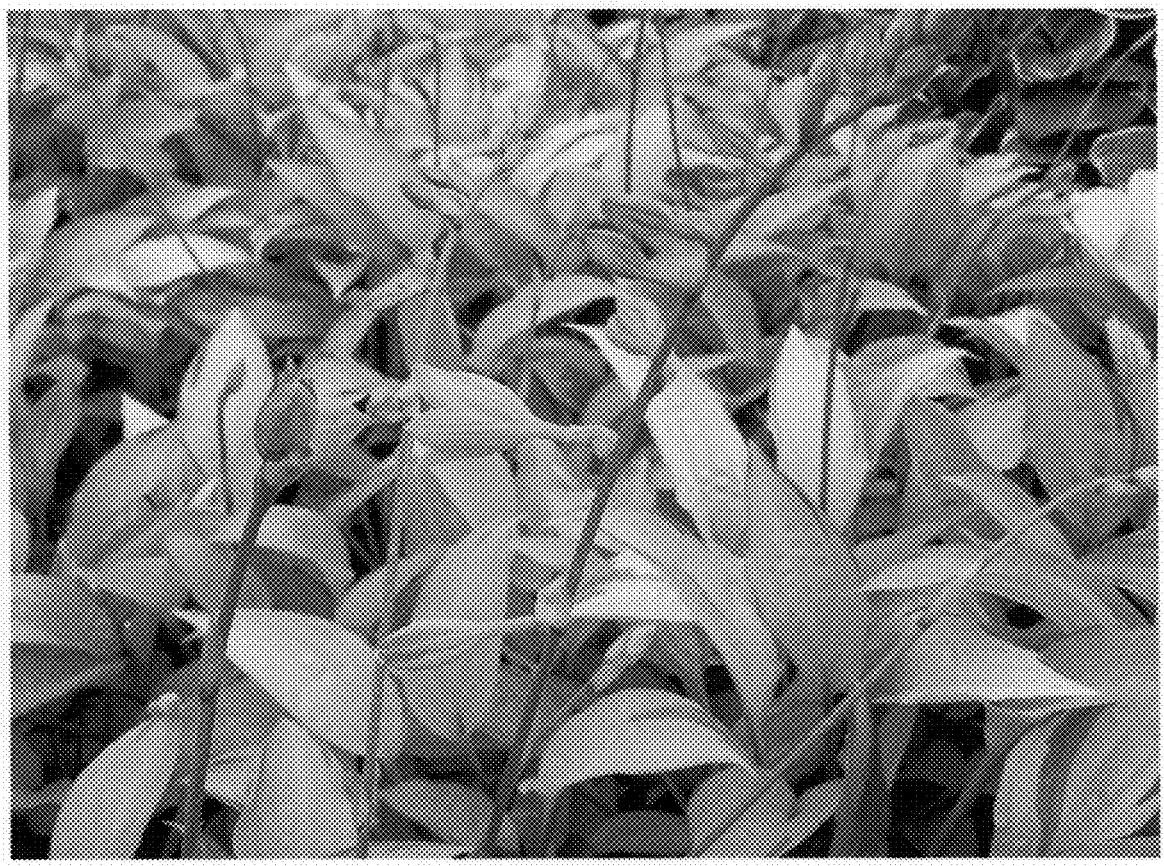

The photograph in FIG. 4 provides a close-up of the new *Hosta's* flowers and buds.

The colors in the photographs are as close as possible with the photographic and printing technology utilized and the color values cited in the Detailed Botanical Description most accurately describe the colors of the new *Hosta.*

DETAILED BOTANICAL DESCRIPTION OF THE PLANT

The following is a detailed description of one year-old plants of the new cultivar as grown outdoors in Ter Aar, The Netherlands. Plants used for data collection were grown under average day temperatures of 10° to 25° C. and average night temperatures of 3° to 14° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—About 4 weeks from mid June to mid July.

*Plant habit.*—Herbaceous perennial, clump-forming, mound of upright foliage.

*Height and spread.*—Reaches about 50 cm in height (including flower scapes) and about 1.5 m in width when mature.

*Hardiness.*—U.S.D.A. Zones 3 to 8.

*Diseases.*—No susceptibility or resistance to diseases has been observed.

*Root description.*—Freely branched, fleshy.

*Propagation.*—In vitro propagation is the preferred method utilizing typical methods for *Hosta*, division are also possible.

*Growth rate.*—Moderate.

Foliage description:

*Leaf shape.*—Ovate.

*Leaf division.*—Simple.

*Leaf base.*—Cordate to obtuse.

*Leaf apex.*—Apiculate.

*Leaf venation.*—Camptodrome pattern, impressed on upper surface and raised on lower surface, color upper surface; 144A on centers and 137B on margins, color lower surface; 148B to 148D on centers and 139A on margins.

*Leaf margins.*—Entire, slightly wavy.

*Leaf attachment.*—Petiolate.

*Leaf arrangement.*—Basal, radiate spirally from base.

*Leaf surface.*—Glabrous on upper surface and lower surface and slightly glossy on upper surface.

*Leaf substance.*—Average.

*Leaf orientation.*—Held nearly upright on upright petioles.

*Variegation pattern.*—Yellow to yellow-green centers and narrow dark green margins.

*Leaf color.*—Emerging foliage, upper surface; N144A and N144B with margin 143A, emerging foliage lower surface; 150B with margin 144B, mature foliage upper surface; 144B, 145C and 1C with margin 137A, 139A and 141B with base dotted with 187C and 187D, mature foliage lower surface; 145B, 145C, 154C and 154D with margin 138A.

*Leaf size.*—Average of 10.4 cm in length and 7.7 cm in width.

*Leaf quantity.*—About 8 per shoot (eye).

*Petioles.*—About 13.2 cm in length, an average of 4 mm in width, glabrous surface, sulcate shape, color upper surface; 145B and heavily dotted with 187B and 187C, color of lower surface; a mixture of 145A and 145B and heavily dotted with 184A and 184B.

Flower scape description:

*Scape shape.*—Round, solid.

*Scape number.*—One per mature eye under normal growing conditions.

*Scape posture.*—Straight, held nearly upright.

*Scape size.*—Average of 50 cm in length and 5 mm in width.

*Scape color.*—144D heavily speckled with color between 59B and 59C.

Scape surface.—Glabrous.

*Leaf bracts.*—Average of 1 per scape, oblong in shape, apiculate apex, truncate base, papery texture and translucent, average of 3.2 cm in length and 8 mm in width, curved inward towards stem, color 161B suffused with N79B at base.

Flower description:

*Inflorescence type.*—Terminal racemes of single bell-shaped flowers on elongated scapes.

*Inflorescence size.*—An average of 5 cm in height and 2 cm in diameter.

*Lastingness of inflorescence.*—About 4 weeks from first opening bloom to fading of last opening bloom, individual blooms last about one day.

*Flower shape.*—Bell-shaped.

*Flower number.*—About 20 per scape.

*Flower internode length.*—Average of 9 mm.

*Flower fragrance.*—None detected.

*Flower bud shape.*—Oval.

*Flower bud size.*—About 3.5 cm in length and 1.1 cm in diameter.

*Flower bud color.*—85A with stripes and shadings of 84A.

*Flower size.*—About 3.5 cm in length and about 1.5 cm in diameter.

*Flower color.*—Blend of 85A and 84A.

*Pedicels.*—About 3 mm in length, 2 mm in diameter, color 145D, surface is glabrous.

*Perianth features.*—Comprised of 6 tepals, 3 interior and 3 exterior, overlapping in expanded region and fused in tube region.

*Tepals.*—Spathulate in shape, about 3.5 cm in length, about 1 cm in width, glabrous surface on upper and lower surface, entire margin, fused base, acute apex, color of outer and inner surface; 85A with stripes and shading of 84A and base of 84D.

*Floral bracts.*—Average of 1 per flower, narrowly ovate in shape, acute apex, truncate base, papery texture and translucent, average of 2 cm in length and 1 cm in width, curved inward towards stem, color of upper and lower surface is 161B suffused and striped with N79B.

Reproductive organs:

*Gynoecium.*—1 Pistil, style is about 3 cm in length, 1 mm in width and 145D in color, stigma is pilose and 145C in color, ovary is superior, compound, composed of 3 locules, oblong in shape, about 4 mm in length and 1.5 mm in width, and 163C in color.

*Androecium.*—6 stamens, filament is 145D in color, 2.7 cm in length, 1 mm in width, recurved and about same length as perianth, anthers are 4 mm in length, 1 mm in width, attachment is versatile, 202A in color, dehiscence is longitudinal, pollen is abundant and 15B in color.

*Fruit/seed.*—Production of seed capsules was not observed.

It is claimed:

1. A new and distinct cultivar of *Hosta* plant named 'Paradise Island' as herein illustrated and described.

* * * * *